United States Patent [19]

Walchle et al.

[11] 4,183,613
[45] Jan. 15, 1980

[54] MICROSCOPE DRAPE AND METHOD OF MAKING SAME

[75] Inventors: David L. Walchle, Ponte Vedra Beach; Richard Pierson, Jacksonville, both of Fla.

[73] Assignee: Xomed, Inc., Jacksonville, Fla.

[21] Appl. No.: 941,773

[22] Filed: Sep. 13, 1978

[51] Int. Cl.² .............................................. G02B 27/00
[52] U.S. Cl. .................................................... 350/65
[58] Field of Search ................... 350/65, 67, 320; 362/294, 267, 362, 804

[56] References Cited

U.S. PATENT DOCUMENTS

| | | | |
|---|---|---|---|
| 3,528,720 | 9/1970 | Treace | 350/65 |
| 3,542,450 | 11/1970 | Terhune | 350/65 |
| 3,585,913 | 6/1971 | Lange | 350/65 |
| 3,698,791 | 10/1972 | Walchle et al. | 350/65 |
| 3,796,477 | 3/1974 | Geraci | 350/65 |
| 4,045,118 | 8/1977 | Geraci | 350/65 |

*Primary Examiner*—Jon W. Henry
*Attorney, Agent, or Firm*—Kinney & Schenk

[57] ABSTRACT

A microscope drape fabricated from a thin soft, relatively inexpensive, plastic film which will melt at temperatures considerably lower than the temperatures which are developed by the illuminating lamp of an operating microscope, is provided with a heat barrier loosely secured to and carried by the inner surface of that portion of the film which, but for the presence of the barrier would be adversely affected by the temperatures induced within the drape adjacent the illuminating lamp of the drape-enshrouded microscope.

12 Claims, 4 Drawing Figures

MICROSCOPE DRAPE AND METHOD OF MAKING SAME

BACKGROUND OF THE INVENTION

1. Field of the Invention

The field of the invention relates to sterilized disposable drapes for enshrouding operating microscopes and their support arms.

2. Description of the Prior Art

U.S. Pat. No. 3,698,791 of D. L. Walchle, et al, discloses a microscope drape which is fabricated from a thin, transparent, relatively expensive sterilizable copolymer film which is capable of withstanding the temperatures induced by the illuminating lamp of an operating microscope, said drape being adapted to completely house an operating microscope including its support arm, whereby heated air cannot escape from the interior of the drape except through the open end thereof which is located remote from the microscope and the operating zone.

U.S. Pat. No. 3,528,720, of H. T. Treace discloses a microscope drape which is fabricated from thin, sterilizable, flexible sheet material which is adversely affected by the temperatures developed by the illuminating lamp of an operating microscope. The drape includes exhaust port means 77 in the upper portion of the drape through which heated air from the interior of the drape is exhausted upwardly of the microscope directly into the operating zone. The said exhaust port is fitted with a disk-like mass 85 of open-cell foam-plastic material which permits a free outward flow of heated air from the interior of the microscope drape and provides baffle or screen means for excluding dust and foreign matter from the interior of the envelope from escaping into the room. The open-cell foam plastic material 85 also provides a surface against which the operating instruments may be wiped to quickly clean same. The exhaust of heated air outwardly through said open-cell material will distribute whatever spores, germs or the like are wiped onto its outer surface directly into the operating zone.

U.S. Pat. No. 3,542,450 of W. I. Terhune discloses a metallic U-shaped heat baffle 11 which is secured to the head assembly of an operating microscope adjacent the lamp housing thereof for preventing a drape fabricated from thin film from contacting the lamp housing or other lamp-heated portions of the microscope. The inner surface of the U-shaped baffle is preferably coated with insulating means in the form of thick foam plastic material 69 69' and 71 adhesively secured thereto. A microscope-encompassing drape is provided with an open, non-obstructed exhaust port grommet 49 in the upper portion thereof for exhausting heated air from the interior of the drape directly into the operating zone of the operating room, immediately above the operating microscope.

U.S. Pat. No. 3,796,477 of J. L. Geraci discloses a microscope drape which is fabricated from thin, transparent sterilizable film, similar to that of U.S. Pat. No. 3,698,791 supra, wherein the drape includes a flexible, resilient, distortable lens housing which is adapted to snugly receive the objective lens ring of the objective lens of an operating microscope.

U.S. Pat. No. 4,045,118 of J. L. Geraci discloses a microscope drape fabricated from a very thin, transparent, heat resistant, sterilizable plastic film which is adapted to completely house an operating microscope including its support arms wherein the drape is provided with unique tubular ocular housing extensions 40 the free outer ends of which terminate in a pull tab which serves to facilitate precise positioning of the tubular housings on the ocular of a microscope and to facilitate removal of said pull tabs which, prior to removal, accurately and effectively position the free outer end of the ocular housing extensions remaining after removal of the tab portion closely adjacent to the outer ends of the eye-pieces of the oculars of the microscope.

U.S. Pat. Nos. 3,698,791; 3,796,477 and 4,045,118 are owned by the assignee of the present application.

SUMMARY OF THE INVENTION

The microscope drape of the present invention is directed to a completely sterile housing in the form of an elongate tubular portion within which an unsterile operating microscope and its horizontal support arms are completely housed in such a manner as to positively preclude the exhaust of heated air into the operating room at a location adjacent the operating zone in the immediate vicinity of the microscope. Those of the prior art microscope drapes which were fabricated from thin, flexible polyethylene material were softer and quiet, in the sense that they did not crinkle when brushed against nor did they produce a glare since the surface thereof was not shiny. However since the film did melt at temperatures in the neighborhood of 100° F. below temperatures produced by the light source of a microscope such drapes could not be used unless special means and precautions were taken to ensure that the drape material was, at all times maintained in sufficiently spaced relationship with respect to the light-source of a microscope as to prevent damage to the drape.

Drapes fabricated from polypropylene film which is capable of withstanding the temperatures induced by the light-source of an operating microscope did not possess the advantages of softness, quietness and lack of glare as possessed by drapes fabricated from polyethylene, and the polypropylene drapes were considerably more expensive than the polyethylene drapes.

The primary object of the subject invention is to provide a heat barrier dissipator in the form of a sheet of foam material which is loosely secured to the inner surface of the drape material whereby to be disposed between the drape material and the light source of a separate microscope.

The effect of the protective sheet is to absorb and dissipate the heat generated by the lamp whereby the temperature of the film in the area of the source of light is maintained at a temperature which is substantially below its melting temperature.

PREFERRED EMBODIMENT OF THE INVENTION

Figure 1:
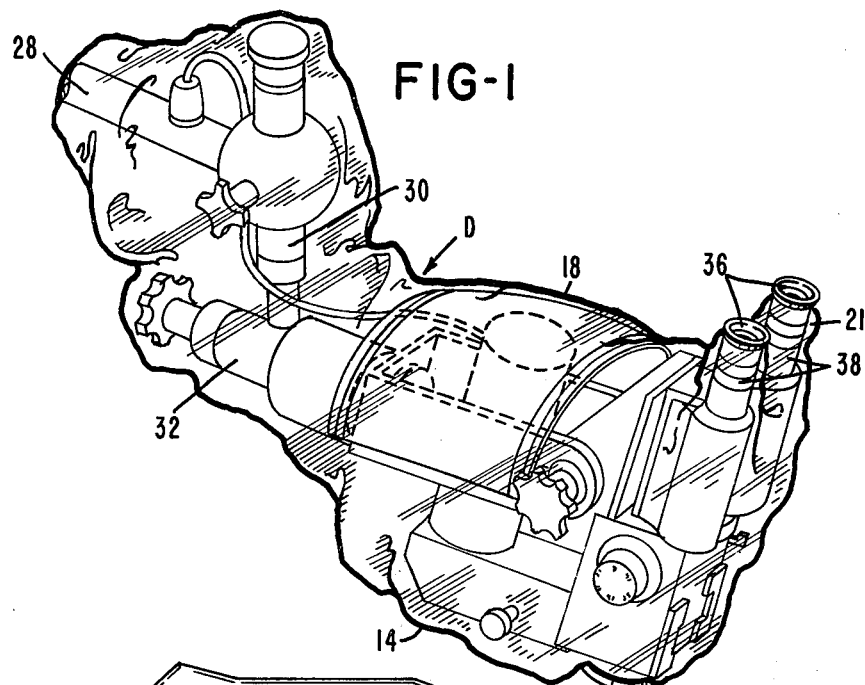
FIG. 1 is a side view of a typical arm-supported microscope housed within a drape of the present invention.
Figure 3:
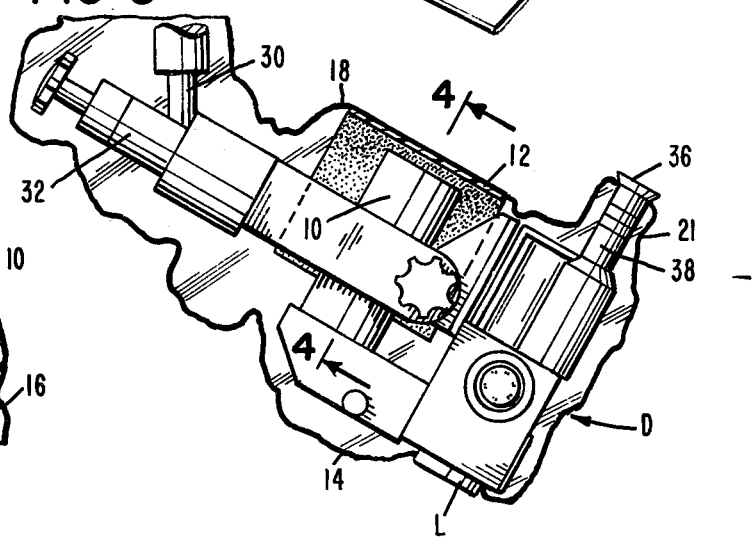
FIG. 3 is a side view of the microscope wherein the drape and its heat barrier sheet are illustrated in section.
Figure 4:
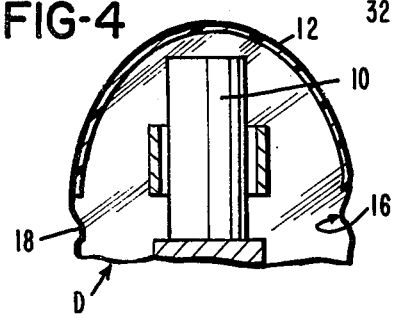
FIG. 4 is a view taken on line 4—4 of FIG. 3.

In FIGS. 1 and 3 a conventional operating microscope has been illustrated as encapsulated within a, sterilized, soft, flexible drape D of the subject invention.

The microscope is, as best illustrated in FIG. 1 of U.S. Pat. No. 3,698,791 mounted relative to an upright or other member by means of a support arm which may comprise a series of adjustably interconnected elements (as illustrated in said patent) which are articulated in such a manner as to enable the user of the microscope to adjust it in any desired position for enabling an observer looking into eyepiece 36 of oculars 38 to examine and study various portions of a patient to be treated and/or operated on, such as, by way of example, the eyes, ears, nose, throat, etc. The microscope includes an objective lens and an illuminating lamp, not illustrated, which is housed within an open-top housing 10 for providing a high intensity source of light for the microscope. The present invention is neither concerned with nor directed to the particular structural details of the operating microscope, since such devices are commercially available as standard articles of commerce.

In FIG. 1 the numerals 28, 30 and 32 denote generally a portion of the adjustably connected elements which comprise a portion of the support arm by which the operating microscope is articulated relative to arm 28 of FIG. 1 of reference U.S. Pat. No. 3,698,791.

Figure 2:
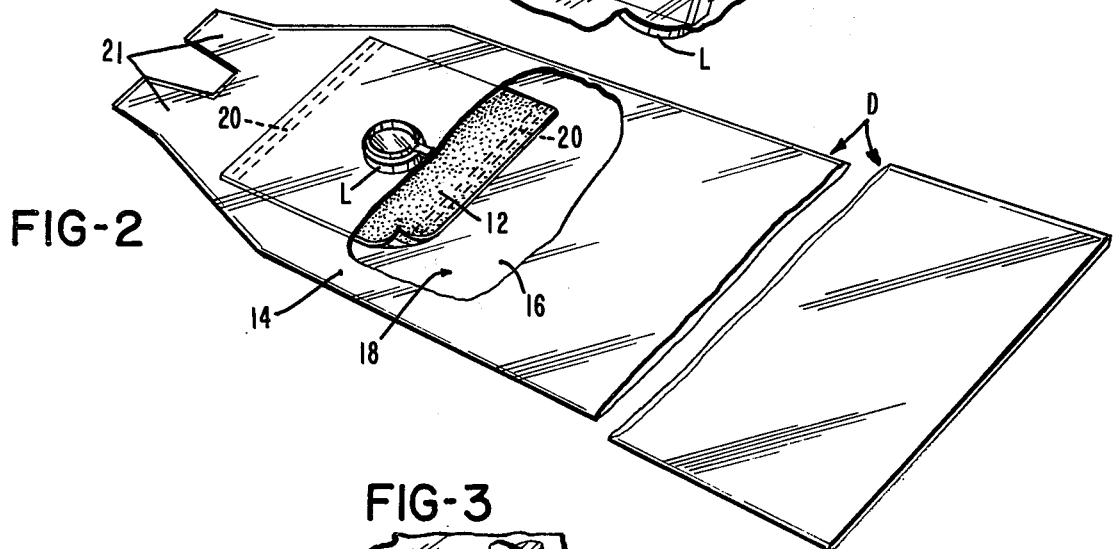
FIG. 2 is a plan view of the drape prior to being associated with a microscope and its support arm.

In FIG. 2 the drape of the present invention is illustrated in a flat, fully extended position as it would appear when ready to be folded into a compact package such as, by way of example, is illustrated in FIG. 2 of the aforesaid reference patent.

In the preferred embodiment of the invention the drape D is fabricated from soft, inexpensive, flexible, sterilizable non-glare polyethylene film approximately 2 mil thick which has a melting point in the neighborhood of 240° F. which is considerably lower than the temperatures developed within the drape and adjacent the illuminating lamp of the microscope.

A heat shield or barrier 12 is loosely secured to the inner surface of that portion of the film of the drape which, but for the presence of said heat shield or barrier, would be adversely affected by the temperatures developed interiorly of the drape adjacent the illuminating lamp. The heat shield or barrier 12, may by way of example, be secured along two of its opposed side edges such as, by means of double-faced adhesive strips 20 whereby those portions of the shield between the attachment strips is disposed in loose, overlying relationship and free of connection to the drape whereby a certain amount of relative movement between the shield and drape may occur incident to manufacture, packaging, shipment, storage and actual use of the drape. Uniformly satisfactory results have been obtained in those instances in which the heat shield or barrier 12 comprises a sheet of open-cell polypropylene foam which is not adversely affected by the temperatures induced within the drape by and adjacent the illuminating lamp of the microscope.

It is believed that the open-cells of the polypropolene sheet permits the highly heated air within the drape, adjacent the illuminating lamp to pass through foam which functions as a heat-sink to effectively reduce the temperature of the air within the drape adjacent the illuminating lamp to temperatures which will not adversely affect the polyethylene film of the drape.

It will be understood that the heated air from the interior of the drape is positively precluded from being discharged into the operating zone adjacent the operating microscope, or into the operating zone, since the drape, when in use, as illustrated in FIG. 1 of U.S. Pat. No. 3,698,791 is open to the atmosphere, only at its open end which is disposed adjacent the means such as upright 22 of the aforesaid reference patent to which the support arm 28 is mounted.

The subject drape combines the soft, flexible, sterilizable, inexpensive, non-glare characteristics of thin polyethylene film, which is adversely affected by the temperatures induced by the illuminating lamp of an operating microscope with the temperature-resisting characteristics of the sheet of open-cell, sterilizable, flexible heat shield or barrier which is not adversely affected by the heat within the drape as developed adjacent and by the illumination lamp of the microscope. The resultant drape has all of the advantages with none of the disadvantages of a drape fabricated entirely from thin polyethylene film.

The subject drape, for the first time, enables drapes for operating microscopes to be fabricated from thin, soft, flexible polyethylene film whereby the heated air is discharged through the open end of the drape at a location remote from the operating microscope, wherein the film of said drape is rendered resistant to or protected from those temperatures adjacent the illumination lamp which would otherwise adversely affect it, by means of a comparatively small sheet of open-cell polypropylene foam approximately ⅛ inch thick.

In FIG. 1 the letter L designates, generally a lens housing of U.S. Pat. No. 3,796,477. In FIG. 2 the numerals 21 designate generally a pair of cylindrical drape extensions which are dimensioned to telescopically engage the oculars 38 of a microscope after which they are tightly secured against and relative to the outer surface of the oculars whereby to preclude the exhaust of heated air from the interior of the drape from around the oculars.

Reference is made to FIGS. 6 through 12 of reference U.S. Pat. No. 3,698,791 for a detailed description of the manner in which the drape of the present invention is secured in enveloping relationship with respect to an operating microscope and its support arms.

Excellent results have been obtained in those instances in which the heat barrier 12 comprises a sheet of 12" by 12" ⅛" open-cell polypropylene foam ⅛" thick as sold by Sur-Seal Gasket Co. of Cincinnati, Ohio.

With particular reference now to FIG. 2 it will be noted that lens housing L is secured to and carried by that portion of the drape which defines the lower portion 14 when associated with a microscope, whereas the heat baffle sheet 12 is attached to the inner surface 16 of the upper portion 18 of the drape at and adjacent that portion of the film which overlies and/or is adjacent the illumination lamp of the microscope, within housing 10.

The resultant drape has all of the advantages and none of the disadvantages of a polyethylene film drape.

What is claimed is:

1. In a disposable drape for positioning over an operating microscope and its support arm wherein the drape is fabricated from a thin, flexible, air-impervious film which is adversely affected by the temperatures induced within the drape adjacent the source of illumination of the microscope, the improvement which comprises;

a sheet of flexible material, characterized by its porous open-cell structure and its ability to withstand the temperatures induced within the drape adjacent the source of illumination of the microscope, positioned in loose contacting relationship against the inner surface of the drape whereby to provide a heat barrier which shields the drape adjacent said source of illumination from attaining temperatures sufficiently high to adversely affect the drape material.

2. A drape as called for in claim 1, wherein the drape is fabricated from polyethylene film and the said sheet comprises open-cell polypropylene foam.

3. A drape as called for in claim 2, wherein the film of the drape is approximately 2 mil thick, and the said sheet is approximately ⅛" thick.

4. A drape as called for in claim 1, wherein the said sheet is substantially rectangular in shape and wherein the said sheet is fastened to a localized area of the inner surface of the film along two of its opposed side edges whereby all other portions of the sheet are disposed in loose, abutting relationship with respect to the inner surface of the film.

5. A drape as called for in claim 4, wherein the said sheet is secured to the film by double faced adhesive strips.

6. The method of preventing a localized area of the thin, flexible film of a microscope drape from melting or being otherwise adversely affected by close proximity to illumination-lamp-induced temperatures in excess of the melting temperature of the film when the drape is disposed in enveloping relationship with an operating microscope, which comprises the step of positioning a sheet of open-cell material which is capable of withstanding the said illumination-lamp-induced temperatures in overlying relationship with that surface of the area of the film which is adjacent the source of the illumination-lamp-induced temperatures.

7. The method as called for in claim 1, wherein substantially the entire area of the sheet is free of direct attachment to the film.

8. The method as called for in claim 1, wherein the film is polyethylene.

9. The method as called for in claim 8, wherein the thickness of the film approximates 2 mils.

10. The method as called for in claim 1, wherein the sheet of open-cell foam material is polypropylene.

11. The method as called for in claim 10, wherein the thickness of the sheet approximates ⅛".

12. The method as called for in claim 1, wherein the sheet is adhesively secured to the said localized area of the film at locations adjacent the peripheral edges of the sheet, and wherein all other portions of the sheet are in overlying relationship with, but free of attachment to the film.

* * * * *